United States Patent
Reinhardt et al.

(10) Patent No.: US 6,282,445 B1
(45) Date of Patent: Aug. 28, 2001

(54) PASSIVE DEFIBRILLATION ELECTRODES FOR USE WITH CARDIAC ASSIST DEVICE

(75) Inventors: Robert W. Reinhardt, Fort Salonga, NY (US); Howard R. Levin, Teaneck; William A. Easterbrook, III, Washington Township, both of NJ (US); Michael Guttman, Rockville, MD (US)

(73) Assignee: Cardio Technologies, Inc., Pine Brook, NJ (US)

( * ) Notice: Subject to any disclaimer, the term of this patent is extended or adjusted under 35 U.S.C. 154(b) by 0 days.

(21) Appl. No.: 09/417,812

(22) Filed: Oct. 14, 1999

Related U.S. Application Data

(60) Provisional application No. 60/104,429, filed on Oct. 15, 1998.

(51) Int. Cl.[7] ........................................ A61N 1/39
(52) U.S. Cl. ................................ 607/3; 607/5
(58) Field of Search ........................ 600/16, 17, 18; 607/3, 5

(56) References Cited

U.S. PATENT DOCUMENTS

| | | | |
|---|---|---|---|
| 4,651,716 | 3/1987 | Forester et al. | 128/1 |
| 4,925,443 | 5/1990 | Heilman et al. | 600/16 |
| 5,498,228 | 3/1996 | Royalty et al. | 600/16 |

*Primary Examiner*—Scott M. Getzow
(74) *Attorney, Agent, or Firm*—Darby & Darby

(57) ABSTRACT

A cardiac support system includes a ventricular assist device adapted to be extended over a portion of a patient's heart to assist the ventricles of the heart to properly contract. One or more stimulating electrodes are mounted on the ventricular assist device in selected locations such that when the ventricular assist device is extended over the heart, the stimulation electrodes are in close proximity to the surface of the heart. The system further includes one or more external pick-up electrodes that receive externally applied energy and conduct that energy to the one or more stimulating electrodes via conductive leads. The external pick-up electrodes may be mounted on the outer surface of the ventricular assist device, or can be located at some other location inside the patient's body. The externally-applied energy will typically be supplied by standard defibrillation paddles located outside of the patient's body. In place of the pick-up electrodes, the stimulating electrodes can be wired directly to, respectively, a source of electrical energy and a ground plate.

32 Claims, 7 Drawing Sheets

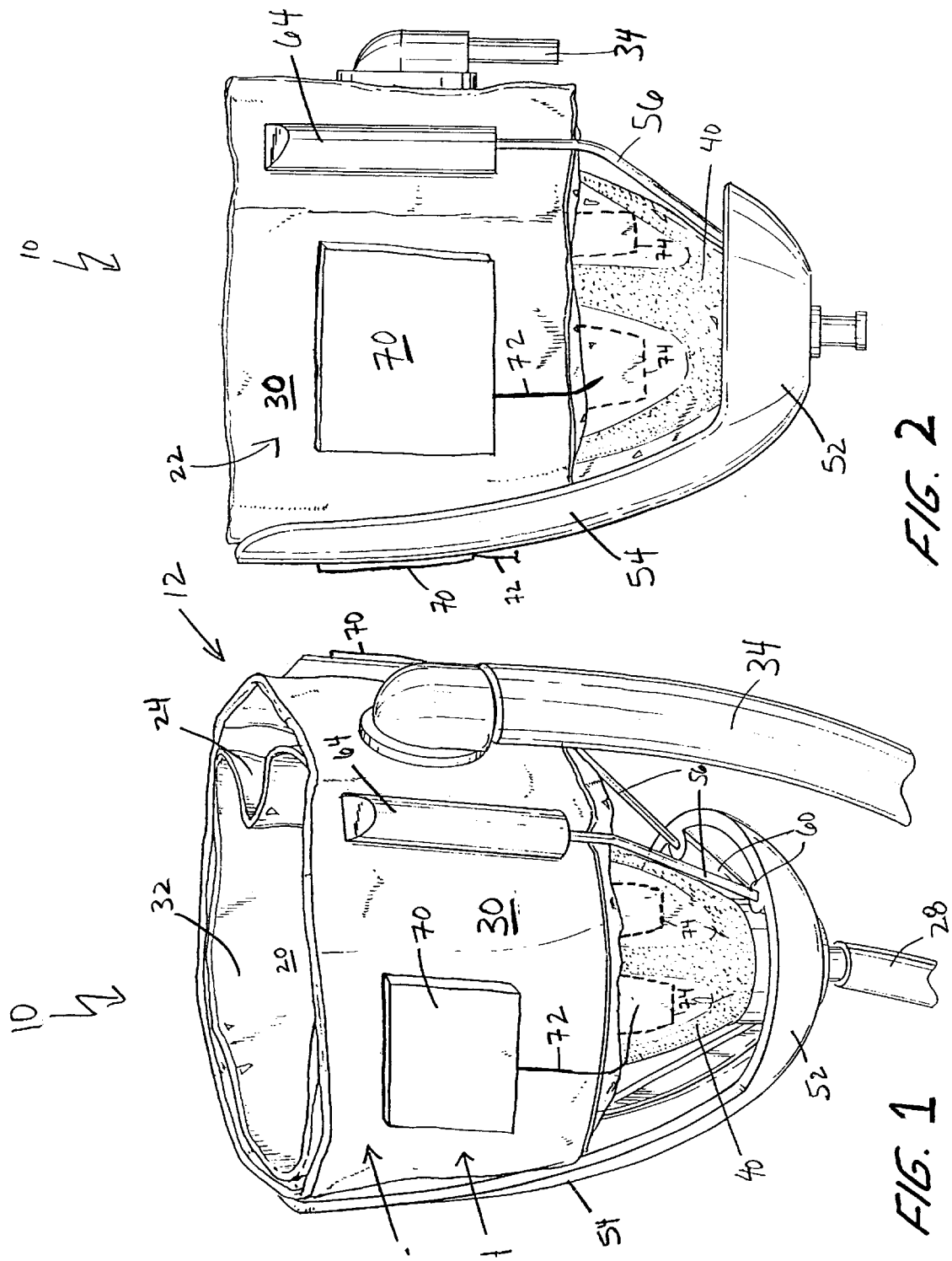

PASSIVE DEFIBRILLATION ELECTRODES FOR USE WITH CARDIAC ASSIST DEVICE

CROSS-REFERENCE TO RELATED APPLICATIONS

This application claims priority pursuant to 35 U.S.C. §119 based upon U.S. provisional application No. 60/104,429 filed Oct. 15, 1998, the entire disclosure of which is incorporated herein by reference.

BACKGROUND OF THE INVENTION

1. Field of the Invention

The present invention relates to a cardiac assist system for helping a heart to properly function. More particularly, the invention relates to a cardiac assist system that applies compressive force to assist the heart in properly contracting, and also applies electrical energy to the heart when needed, such as when the heart is fibrillating.

2. Discussion of the Related Art

The human heart is a very complicated organ that relies on both mechanical and electrical operation to properly function. Over time, the electrical pathways in the heart (which sequentially cause the atria and ventricles to contract) may fail, thereby causing the heart to lose its rhythm, which is known as arrhythmia. In that event, the ventricles will contract at improper times, and as a result the quantity of blood output by the heart decreases. In addition, in some failing hearts the heart muscles do not sufficiently contract the ventricles, also resulting in a dangerous reduction in the amount of blood flow. Furthermore, some hearts occasionally fibrillate (i.e., the muscles of the heart rapidly and irregularly contract), resulting in a lack of synchronism between the heart beat and pulse beat. If not remedied, all of these ailments can cause serious problems, including death.

Numerous attempts have been made to assist diseased or failing hearts by applying external pressure directly to the heart. One such example is direct manual compression of the heart by a person's hand during open chest cardiopulmonary resuscitation. Often, however, the patient requires cardiac or circulatory support for extended periods of time, such as hours, days, or even weeks, and it is quite difficult, if not impossible, for medical personnel to apply a rhythmic pulsating pressure for such an extended period of time. Further, it is difficult, if not impossible, to apply by hand a uniform compressing force to a significant portion of the exterior ventricle surface of the heart. Moreover, the chest should not be opened for extended periods of time because of, among other things, the increased risk of infection. As such, manual manipulation of the heart is not a solution to the problem in most cases.

To overcome this problem, different types of mechanical devices have been developed which intermittently apply external pressure directly to the heart. Some of these devices utilize an inflatable liner that surrounds the heart. For example, U.S. Pat. No. 5,119,804 to Anstadt discloses a cup that is provided with an elastomeric liner. The heart is held in place within the liner, which is cyclically inflated and deflated to apply external pressure to the heart.

In addition, it has been found that these inflatable liner devices can act as electrical insulators to insulate the heart from externally applied energy, such as the energy from defibrillation paddles. Therefore, when such a device is in place over the heart (which can be on the order of days or even weeks), the heart in many instances cannot be defibrillated, if the need arises. It is believed that the polymer material of the liner device, and the air in the liner when it is inflated, act as insulators around the heart, preventing the defibrillation current from reaching the heart.

Accordingly, it will be apparent that there continues to be a need for a cardiac assist system that assists the ventricles to contract in a natural and safe manner, and which also can apply electrical energy to the heart, for example in cases where the heart is fibrillating. The present invention addresses these and other needs.

SUMMARY OF THE INVENTION

Briefly, and in general terms, the present invention in one illustrative embodiment is directed to a cardiac assist system that includes a ventricular assist device adapted to be extended over a portion of a patient's heart to assist the ventricles of the heart to contract. One or more passive, stimulating electrodes are mounted on the ventricular assist device in selected locations, such that when the ventricular assist device is extended over the heart, the stimulating electrodes are in close proximity, or contact, with the surface of the heart. The system further includes one or more external pick-up electrodes that collect externally applied energy and conduct that energy to the one or more stimulating electrodes via conductive leads. The external electrodes may be mounted on the outer surface of the ventricular assist device, or can be located elsewhere inside the patient's body, or even at a location outside of the patient's body. The externally-applied energy will typically be supplied by standard defibrillation paddles located outside the patient's body. Thus, with the present invention, externally applied defibrillation energy can be applied to the heart, even when an insulating ventricular assist device is extended over the heart.

Thus, in one illustrative embodiment the present invention comprises a defibrillation system for defibrillating a heart, including at least one pick-up electrode located inside a patient's body, the pick-up electrode being responsive to the application of external energy to the patient to collect at least a portion of the energy, and at least one stimulating electrode in electrical communication with the at least one pick-up electrode, the stimulating electrode being disposed at a predetermined location adjacent to the heart and responsive to receipt of collected energy from the pick-up electrode to apply the energy to the heart.

In another illustrative embodiment the present invention is directed to a cardiac assist system comprising: a ventricular assist device adapted to be placed over at least a portion of the heart and operative to intermittently apply a compressive force on the ventricles of the heart to force the ventricles to contract; at least one stimulating electrode connected to the ventricular assist device at a predetermined location thereon to be located adjacent the heart when the ventricular assist device is placed over the heart; and at least one pick-up electrode electrically connected to the at least one stimulating electrode, the pick-up electrode being operative to collect externally applied energy and to conduct the externally applied energy to the stimulating electrode to defibrillate the heart.

The present invention, in yet another illustrative embodiment, is directed to a method of defibrillating a human heart, comprising: applying defibrillation energy to a patient from a location external to the patient; receiving the externally applied energy at one or more electrodes inside the patient's body and spaced from the heart; and conducting the received energy to one or more electrodes in contact with the patient's heart to apply the energy to the heart.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings wherein:

FIG. 1 is a perspective view of a cardiac assist device according to one illustrative embodiment of the present invention;

FIG. 2 is a side view of the cardiac assist device shown in FIG. 1;

DETAILED DESCRIPTION OF THE PREFERRED EMBODIMENTS

Figure 3:
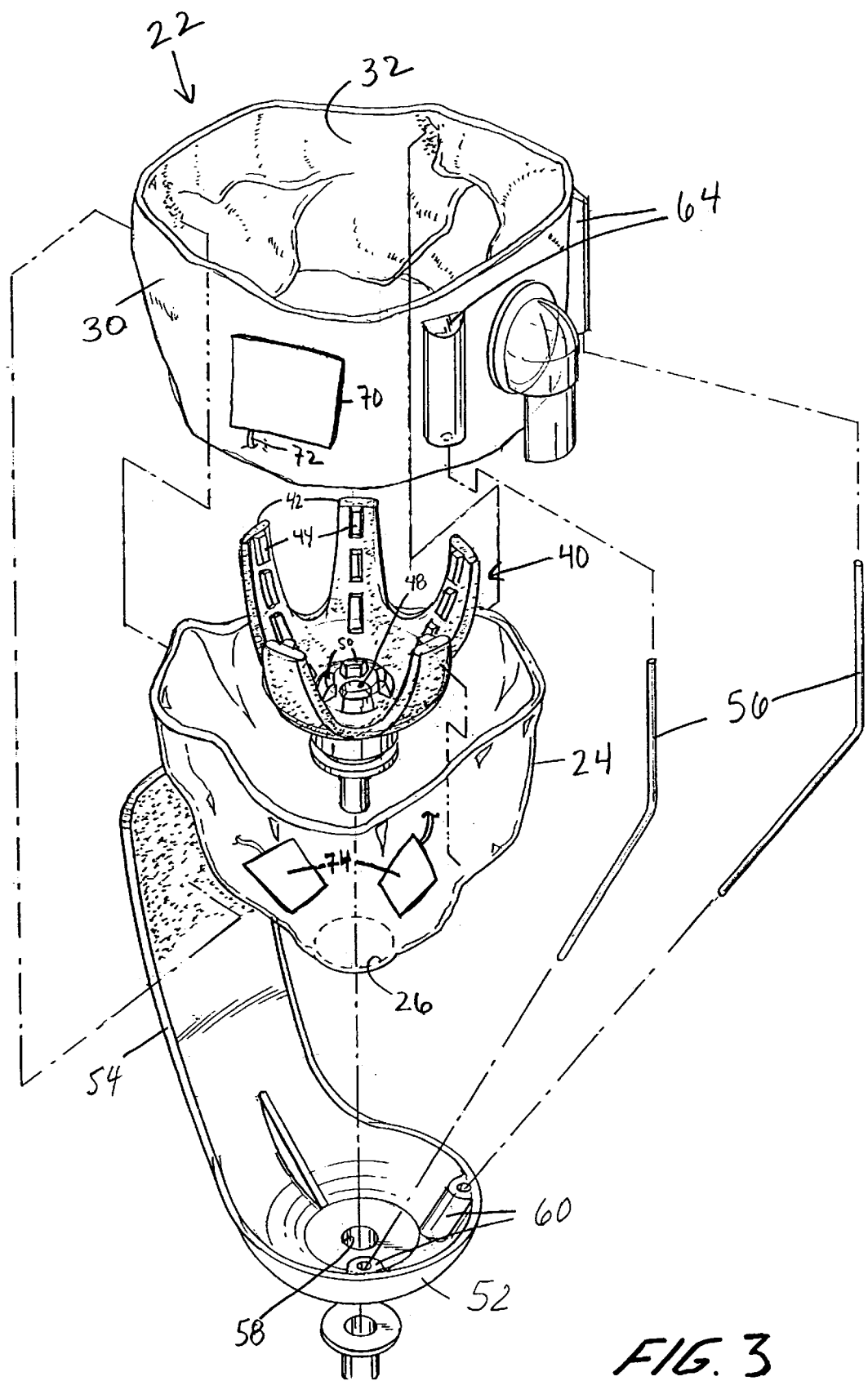
FIG. 3 is an exploded perspective view of the cardiac assist device shown in FIG. 1.

Referring now to FIG. 1, one illustrative embodiment of a cardiac assist device 10 according to the present invention is shown. The cardiac assist device 10 is operative to intermittently apply a compressive force against the ventricles so that they properly contract, and which also collects externally applied electrical energy and delivers that energy to the heart for defibrillation, pacing, and other suitable purposes. The cardiac assist device comprises, generally, a ventricular assist device 12, in the form of a ventricular cuff, which is actuated by a source of pressurized fluid (not shown) to cyclically inflate and deflate to thereby intermittently compress the ventricles. The cardiac assist device further includes an electrical collection and delivery system 14 which is operative to collect electrical energy coming from an external source, for example from defibrillation paddles outside the patient's body, and to deliver the collected electrical energy to the patient's heart to perform defibrillation, pacing, or other functions.

The illustrative embodiment of the ventricular assist device 12 shown in the figures is described in greater detail in co-pending U.S. patent application Ser. No. 60/098,130, entitled "METHOD AND APPARATUS FOR ASSISTING A HEART TO PUMP BLOOD", and filed on Aug. 27, 1998, assigned to the assignee of the rights in the present invention, the disclosure of which is hereby expressly incorporated by reference. It will be apparent that the cardiac assist device 10 of the present invention can incorporate any suitable ventricular assist device, for example, the other types of ventricular assist devices shown in the above-mentioned and expressly incorporated patent application, and that the device 12 shown in the figures is exemplary of one such device. In general, the ventricular assist device (or cuff) comprises an upwardly opening receptacle defining an interior chamber 20 sized for making a relatively close fit about at least a portion of a patient's heart. The chamber is defined by an annular inflatable bladder 22 and an upwardly opening suction membrane 24 disposed inwardly of the bladder. The suction membrane includes a central opening 26 (FIG. 3) formed in the lower end thereof that is engaged to one end of a vacuum tube 28 for fluid communication therebetween. The other end of the vacuum tube is connected to a vacuum source (not shown) that is operative to draw air through the vacuum tube. The suction membrane is preferably connected at its upper end to the upper end of the bladder by means of UV adhesive, cyanoacrylate, heat sealing, or other suitable means. Thus, the cuff may be extended over the ventricles of the heart, the vacuum tube connected to the vacuum source, and the vacuum source actuated to withdraw air from the chamber 20 to create a partial vacuum within the chamber, which causes the suction membrane to be drawn radially inwardly and into secure engagement with the heart.

The bladder 22 is preferably made from a combination of biocompatible, reinforced and non-reinforced polyurethane, or other elastic polymers. In one embodiment the polyurethane defines a fluid impermeable layer that is reinforced with a non-stretchable reinforcing layer, for example, a polyester weave. The outer wall 30 of the bladder is preferably thicker, stiffer, or of a higher durometer than the bladder's inner wall 32, or incorporates other mechanical means, such as reinforcing members, to resist radial outward expansion of the bladder. The outer wall is further formed with one or more openings 33 (FIG. 4) that are in fluid communication with first ends of respective flexible fluid lines 34. The respective second ends of the fluid lines are connected to one or more sources of pressurized fluid (not shown) to selectively inflate the bladder. In the illustrative embodiment shown, when the bladder is deflated the inner wall of the bladder folds in upon itself while remaining in relatively close proximity to the heart. Then, as the bladder is inflated, the inner wall at least partially unfolds as it is driven radially inwardly to uniformly engage the portion of the heart that is contained within the cuff 12. In this manner, the bladder need not stretch to engage the heart, resulting in a substantially uniform application of force to the ventricle outer walls, without any significant loss due to transmural pressure in the inner wall of the bladder, because the bladder is not stretched as it is inflated. In addition, because the bladder does not stretch, the heart is not contorted into a generally hourglass shape when the bladder is inflated and comes into contact with the heart.

Figure 4:
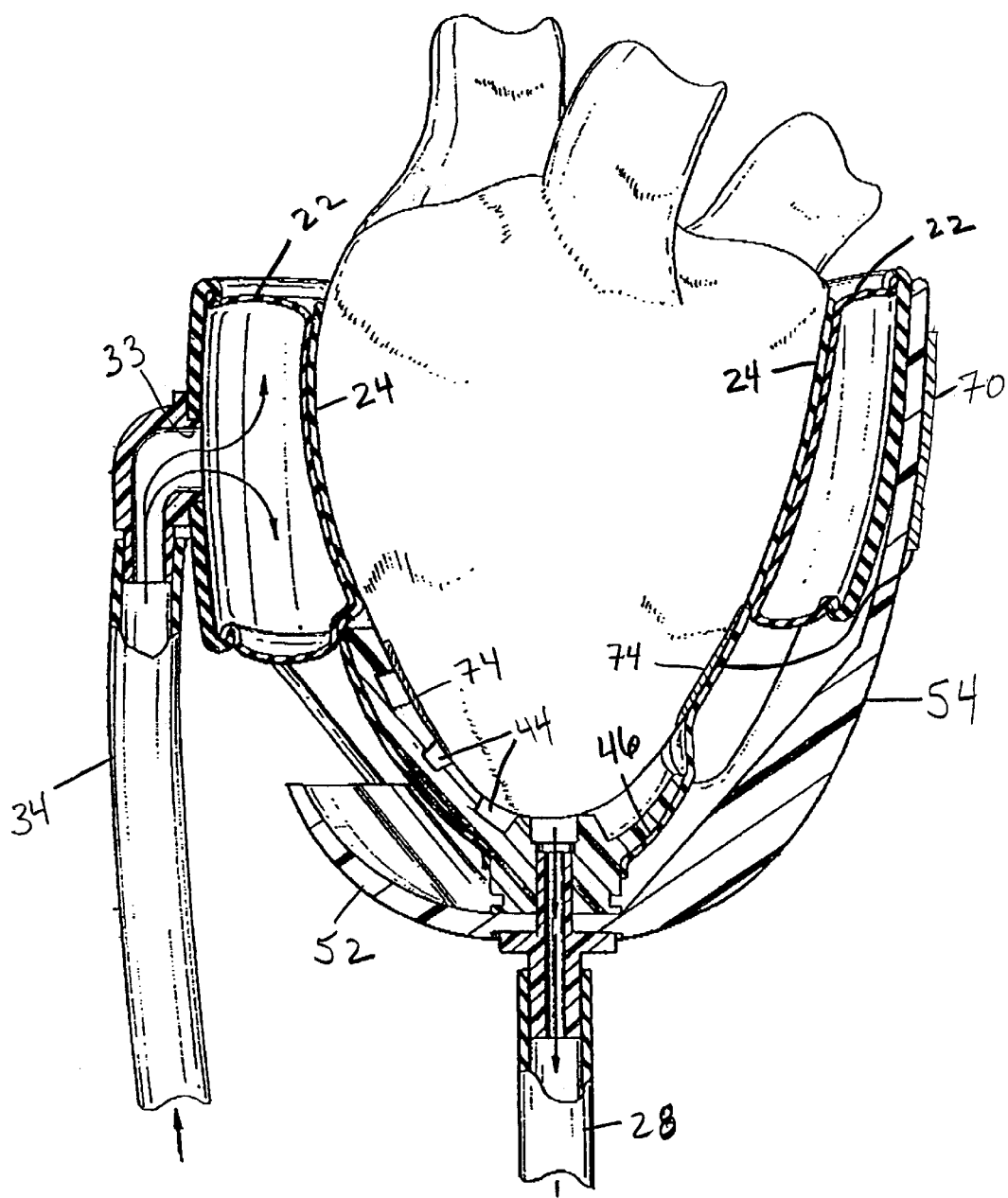
FIG. 4 is a cross-sectional side view of the cardiac assist device shown in FIG. 1.

The ventricular cuff 12 further includes a flexible cleated finger assembly 40 for releasably engaging the outer surface of the heart (FIGS. 3 and 4). The flexible cleated finger assembly is disposed inwardly of the suction membrane 24, such that when the suction membrane is drawn inwardly against the heart, the fingers are driven into contact with the patient's heart. The finger assembly is preferably molded of a very flexible polymer, such as polyurethane, silicone, TPE, etc., and is connected to the inner surface of the suction membrane 24 by means of a UV cyanoacrylate or other adhesive, heat sealing, or other suitable means. The finger assembly includes plural fingers 42 (FIG. 3), for example five, each of which includes plural projecting cleats 44 to engage the outer surface of the heart (FIG. 3). The finger assembly further includes a base 46 (FIG. 4) engaged to the suction membrane 24 and formed with a central opening 48 (FIG. 3) aligned with the opening in the suction membrane for fluid communication therethrough. The base also includes plural raised cleats 50 (FIG. 3) which surround the opening 48 to prevent the heart tissue from plugging the opening when the vacuum source is actuated. The cleats and fingers cooperate to define plural fluid flow paths to allow fluid to be drawn from substantially the entire chamber through the vacuum line 28. In this manner, the holding force is distributed over a large portion of the surface of the heart rather than being concentrated at the apex of the heart, resulting in a more secure engagement of the cuff to the patient's heart without a large force being applied to a small area of the heart.

Referring to FIG. 3, the ventricular cuff 12 further includes an apical reinforcing support assembly including a spatula 52, a backplate reinforcement 54, and a pair of supporting rods 56. The spatula is preferably formed of semi-rigid polymer such as in polyurethane, silicone, TPE, etc. that is securely engaged to the bottom ends of both the finger assembly 40 and the suction membrane 24. The spatula thus serves to hold the finger assembly and suction membrane in place relative to the bladder 22. The spatula is formed with a central opening 58 for extension therethrough of the vacuum line 28.

The backplate reinforcement 54 is preferably formed integral with the spatula 52 and is also preferably formed of semi-rigid polyurethane, silicone, TPE, etc. The backplate reinforcement is connected to the outer wall of the bladder 22 by means of a layer of adhesive, by heat sealing, or the like. The backplate is designed for alignment with the inferior portion of the heart, and thus the portion of the bladder aligned with the backplate is preferably not inflatable, although it may be inflatable.

The supporting rods or stylettes 56 are in the form of curved segments of a non-flexible material such as titanium, stainless steel, polycarbonate, engineering plastic, or the like. The respective bottom ends of the rods are received in respective upwardly opening receptacles 60 formed in the spatula 52. The rods angle upwardly and outwardly from the spatula, and then turn to extend upwardly and terminate in respective upper ends that are received in respective stylette caps 64 that are bonded to the outer wall of the bladder 22 by means of UV adhesive, cyanoacrylate, heat sealing, or other suitable means. The receptacles are preferably formed of a flexible polymer, such as polyurethane, silicone, TPE, etc. or the like. The rods are preferably spaced approximately 90°–120° apart. The rods provide support for the bladder as the bladder and suction membrane 24 are extended over the heart, and cooperate with the backplate reinforcement to facilitate extension of the bladder and suction membrane over the heart.

Figure 5:
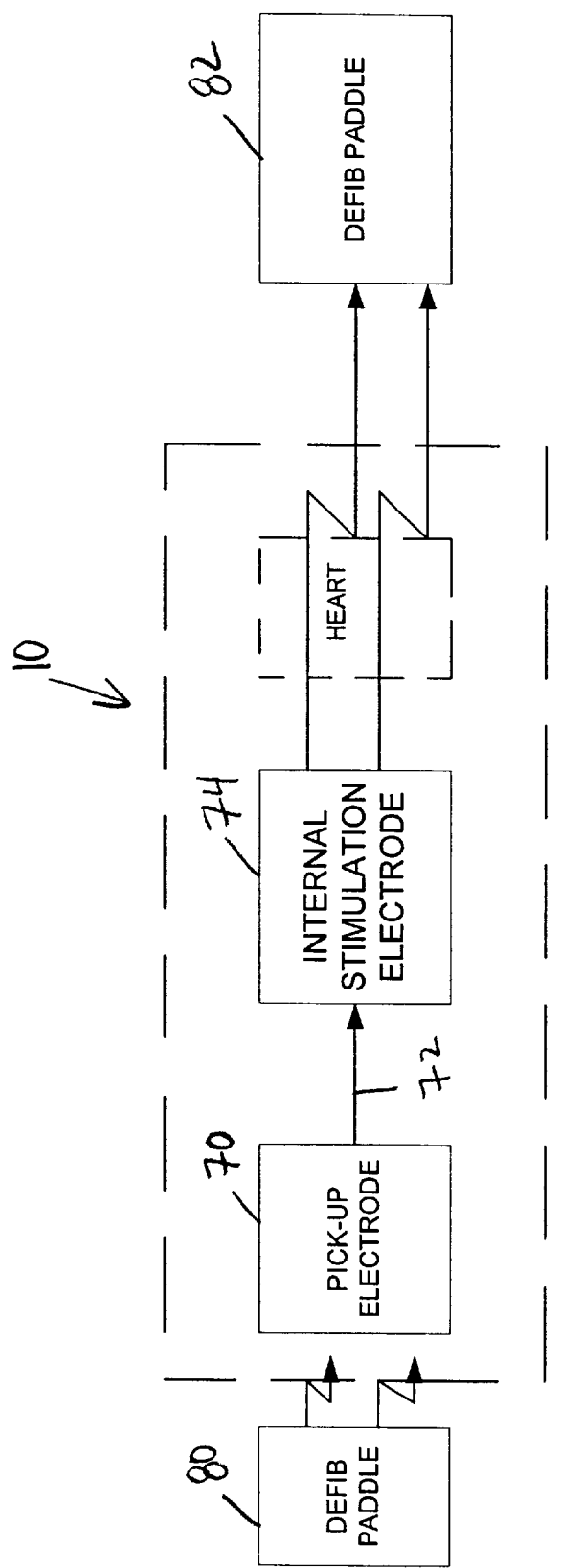
FIG. 5 is a block diagram of components included in the cardiac assist device of FIG. 1.
Figure 6:
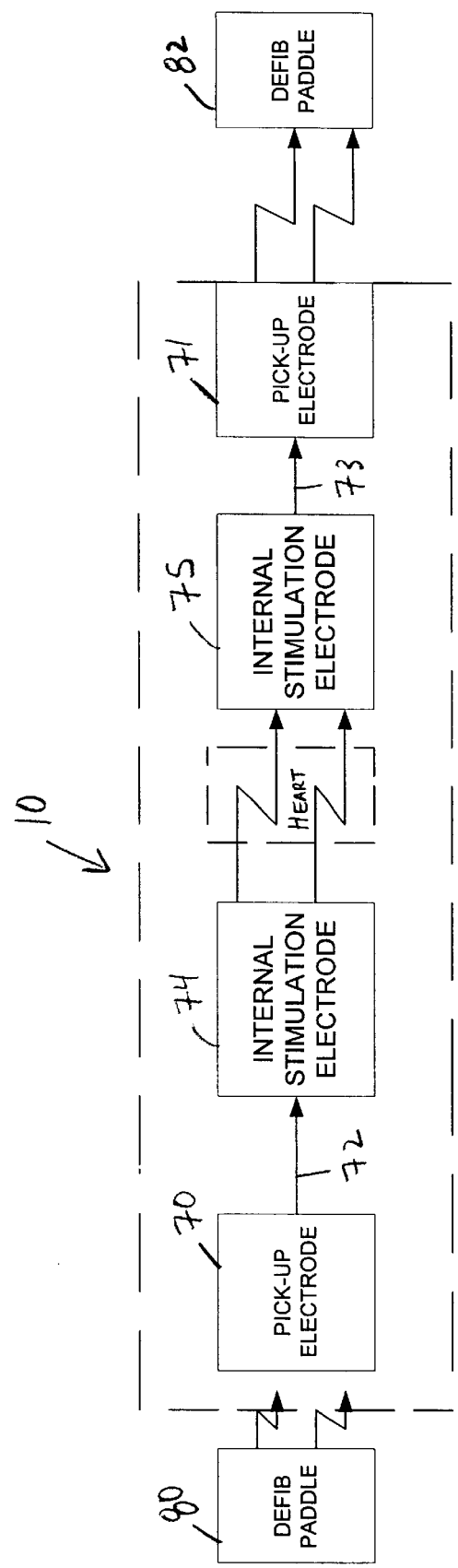
FIG. 6 is a block diagram of components included in another illustrative embodiment of the cardiac assist device of the present invention.

Referring now primarily to FIGS. 5 and 6, the electrical collection and delivery system 14 will be described in detail. The electrical system includes one or more external, "pick-up" electrodes 70 and 71 which, in one illustrative embodiment, are located inside the patient's body. The electrodes are formed having relatively large cross-sectional dimensions to act as pick-ups for externally applied electrical energy, for example defibrillation energy from conventional defibrillation paddles. The external electrodes 70 and 71 may be mounted to the outside surface of the ventricular assist device 12, as shown in FIGS. 1 and 2, or may be disposed within the patient's body at a selected location spaced from the ventricular assist device. The external electrodes are connected to respective electrical leads 72 which serve to conduct electrical energy collected by the external "pick-up" electrode(s).

In one illustrative embodiment, at least one of the external electrodes 70 is mounted on the ventricular assist device 12, preferably over the backplate reinforcement 54 (FIG. 4). Due to the shape of the heart and the conventional sites on a patient's body where defibrillation paddles are typically placed, the backplate reinforcement will typically be facing directly toward the site where the high-potential defibrillation paddle 80 is placed against the patient's body during a defibrillation procedure. Thus, placement of the external electrode 70 over the backplate reinforcement makes it likely that the pick-up electrode will receive a substantial portion of the externally applied energy.

The electrical collection and delivery system 14 further includes one or more stimulation electrodes 74 and 75 mounted on or otherwise situated against the inside surface of the ventricular assist device 12. The stimulation electrodes may be mounted at any suitable interior location such that when the ventricular assist device 12 is placed over the heart, the electrodes are brought into close proximity to, or contact with, the heart. Examples of suitable locations are on the friction fingers 42, on the base of the suction membrane 24, on the internal rim of the bladder 22, on the inner surface of the suction membrane 24 in between the friction fingers 42, and the like. One or more of the stimulation electrodes are connected to the electrical leads 72 to receive the electrical current collected by the external pick-up electrodes 70 and to apply that current to the heart to stimulate the heart, as would the conventional defibrillation paddles.

In one preferred embodiment, the stimulation electrodes 74 are mounted on the inside surface of the suction membrane 24. As described above, when the vacuum source is actuated, the suction membrane is drawn radially inwardly and into engagement with the heart. With the stimulation electrodes mounted on the inside surface of the suction membrane, the stimulation electrodes are automatically driven into contact with the heart upon activation of the vacuum source. As such, the vacuum source and suction membrane do away with the need for more traditional, and undesirable, attachment methods, such as suturing and adhesive methods. Instead of being mounted on the inside surface of the suction membrane, the stimulation electrodes can be placed against the inside surface of the suction membrane, so that when the ventricular assist device is extended over the heart, the electrodes are sandwiched between the suction membrane and the heart tissue.

In addition, because the suction membrane 24 is made of flexible material to configure to the shape of the heart so that it can make a close fit about the heart, the stimulation electrodes 74 and 75 are preferably formed of a flexible, resilient, and conductive material so that they may also assume a suitable configuration to complement the configuration of the heart. With the stimulating electrodes in contact with the heart, they can be used as ECG pick-ups as well, as described in greater detail below in connection with FIGS. 7 and 8.

In one preferred embodiment, the cardiac assist system 10 includes one external pick-up electrode 70 and one internal stimulation electrode 74 (FIG. 5), with the external electrode and stimulation electrode coupled through an electrical lead 72. Thus, the pick-up electrode 70 receives electrical energy from the high-potential defibrillation paddle 80, which energy is then conducted through the lead 72 to the coupled stimulation electrode 74. The electrical energy then passes from the ventricles of the heart, up through the atria to the chest cavity, providing an electrical path to the grounded or low-potential defibrillation paddle 82 or other low-potential body electrode attached to the patient's skin, or to a ground plate (not shown) upon which the patient is laid, all of which are well known to those skilled in the art.

In a second illustrative embodiment of the cardiac assist device 10, shown in FIG. 6, the device includes a pair of external electrodes 70 and 71, one of which serves as a high-potential pick-up electrode 70 and the other of which acts as a receiver 71 for energy that has passed through the heart and which transmits that energy to the low-potential defibrillation paddle 82, ground plate, or the like (FIG. 6). The device also includes a pair of internal stimulation electrodes 74 and 75 which are connected to the respective external electrodes via conductive leads 72 and 73. Thus, the stimulation electrode 74 connected to the high-potential pick-up electrode 70 defines a high-potential stimulation electrode, while the stimulation electrode 75 connected to the other external electrode 71 defines a low-potential stimulation electrode. In operation, electrical energy is applied to the body by the high-potential defibrillation paddle 80, which is collected by the pick-up electrode 70. The collected energy is conducted to the high-potential stimulation electrode 74 via the lead 72. The energy then passes through the heart to the low-potential stimulation electrode 75, preferably mounted on the inside surface of the suction membrane 24. The energy is then conducted to the low-potential external electrode 71 through the lead 73, where it is transmitted through the patient's body to the low-potential defibrillation paddle 82, ground plate, or the like.

It will be apparent that the embodiment shown in FIG. 6 overcomes any insulating problems created by the ventricular assist device 12. The externally applied energy is collected outside of the ventricular assist device 12 by the electrode 70, and is conducted to the first internal stimulation electrode 74, thereby bypassing the ventricular assist device. The applied energy is collected by the low-potential stimulation electrode 75 and is conducted to the low-potential electrode 71 outside of the ventricular assist device, thereby bypassing the ventricular assist device.

It will also be apparent that the cardiac assist device 10 of the present invention can be incorporated into a cardiac system which electrically monitors the patient's heart, intermittently and automatically actuates the ventricular assist device 12 at selected times, and receives externally applied defibrillation energy and delivers that energy to the patient's heart when necessary. Such a system is disclosed in co-pending U.S. patent application Ser. No. 60/107,105, entitled "CARDIAC ASSIST SYSTEM AND METHOD THEREOF", filed on Nov. 14, 1998, assigned to the assignee of the rights in the present invention, and which is incorporated herein by reference.

In use, the cardiac assist device 10 may be maneuvered into position over at least a portion of a patient's heart (FIG. 4), thereby positioning the stimulation electrodes 74 and 75 in close proximity to, or contact with, the patient's heart. The ventricular assist device 12 may then be connected to a suitable vacuum source via the vacuum tube 28, and to a suitable source of pressurized fluid via the line 34. The vacuum source is then actuated to cause the suction membrane 24 to collapse about the heart and thereby securely engage the heart, which causes the stimulation electrodes 74 and 75 to come into contact with the heart, in the event the electrodes are mounted on the inside surface of the suction membrane. The suction membrane forces the electrodes against the heart tissue, such that there is no relative movement between the heart and electrodes. The source of pressurized fluid is then intermittently activated to apply a compressive force to the ventricles of the heart and thereby assist the heart to properly contract.

In the event the patient's heart should begin to fibrillate or otherwise require the application of one or more electrical stimulating pulses, the electrical system 14 is provided. The clinician must simply perform the usual procedure, for example applying energized defibrillation paddles 80 and 82 to the patient's body. The energy from the high-potential paddle 80 proceeds toward the low-potential paddle 82, and is collected by the pick-up electrode 70, which is the path of least resistance. The collected energy is conducted along lead 72 to the internal stimulation electrode 74. The energy then passes through the heart to the other stimulation electrode 75, and is conducted to low-potential electrode 74, where it passes through the patient's body to the low-potential defibrillation paddle 82. The operation of the embodiment shown in FIG. 5 is similar, except that the energy passes through the heart and chest cavity directly to the low-potential defibrillation paddle 82.

Figure 7:
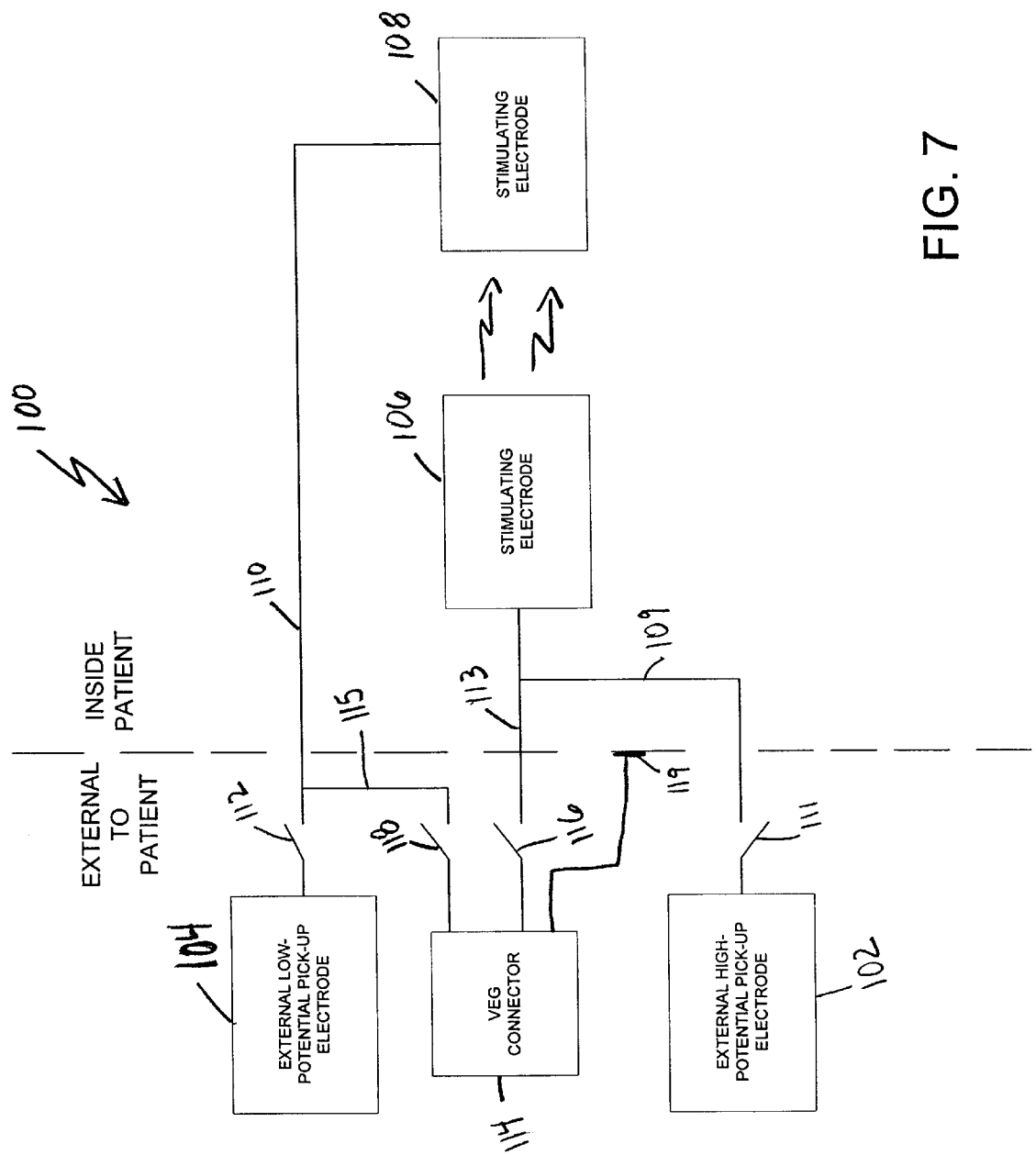
FIG. 7 is a block diagram of components included in yet another illustrative embodiment of the cardiac assist device of the present invention.

Referring now to FIG. 7, there is shown another illustrative embodiment of the cardiac assist system 100 of the present invention. The system includes a pair of pick-up electrodes 102 and 104, which in this embodiment are located outside of the patient's body. The electrodes are connected to respective stimulating electrodes 106 and 108 located inside the patient's body via respective leads 109 and 110. The stimulating electrodes are preferably mounted on the inside surface of the suction membrane 24 as described above, or at any other suitable location. Switches 111 and 112 are interposed between the respective pick-up and stimulating electrodes.

The stimulating electrodes 106 and 108 are also electrically connected to a VEG connector 114 via respective leads 113 and 115 and switches 116 and 118. The VEG connector is also connected to a standard ECG surface electrode 119 which is applied to the patient's skin and serves as a reference voltage for the VEG measurements. Thus, the stimulating electrodes 106 and 108 can be used to either defibrillate the heart, or to sense the heart's electrical activity. In the heart sensing mode, the switches 111 and 112 are opened, and the switches 116 and 118 are closed. The electrodes, by being strategically placed on the cuff 12, are in close proximity to, or in contact with, the heart, and therefore sense the electrical activity of the heart, and conduct that activity as electrical signals to the VEG connector for processing, as is well known to those skilled in the art.

When the system 100 is to be used to defibrillate the heart, the switches 116 and 118 are opened, and the switches 111 and 112 are closed. Electrical energy is then supplied to the high-potential pick-up electrode 102, which conducts the energy to the stimulating electrode 106. The energy then passes through the heart to the low-potential stimulating electrode 108, which conducts the energy to the low-potential pick-up electrode 104.

In place of the pick-up electrodes 102 and 104, the stimulating electrodes 106 and 108 could be wired directly to, respectively, a source of electrical stimulating energy and to a ground plate or the like. Thus, the pick-up electrodes may be removed in this embodiment.

Figure 8:
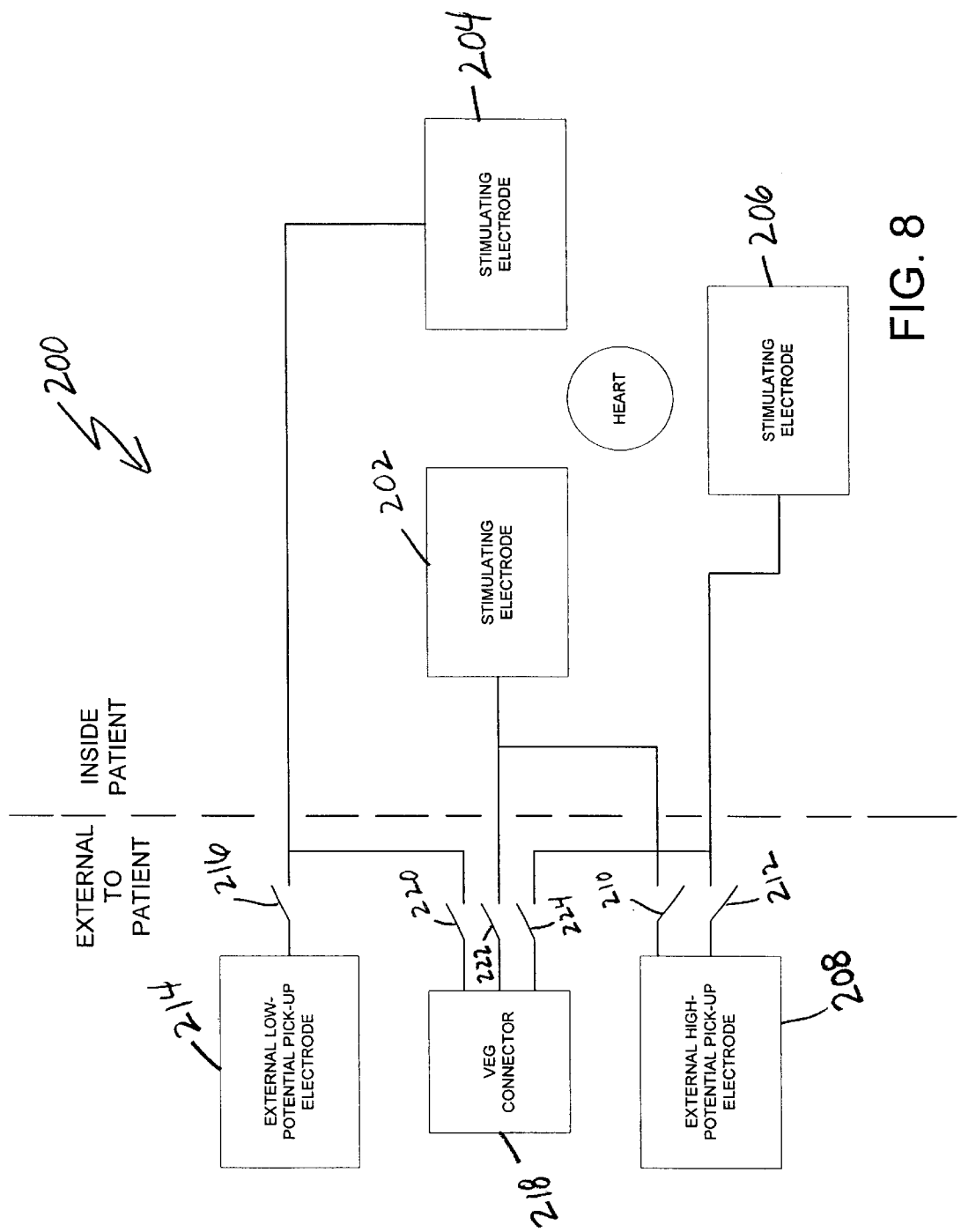
FIG. 8 is a block diagram of components included in still another illustrative embodiment of the cardiac assist device of the present invention.

Referring to FIG. 8, there is shown another illustrative embodiment of the system 200 of the present invention, which is similar in many respects to the system 100 of FIG. 7. The system 200 includes three stimulating electrodes 202, 204, and 206, preferably spaced equiangular around the circumference of the cuff 12 and mounted on the inside surface of the suction membrane 24. Two of the stimulating electrodes 202 and 206 are connected to a high-potential pick-up electrode 208 via switches 210 and 212. The other stimulating electrode 204 is connected to a low-potential pick-up electrode 214 through switch 216. Again, the pick-up electrodes 208 and 214 are located outside of the patient's body, and can be replaced by wires that directly connect the various stimulating electrodes to a source of electrical energy and ground, respectively.

Each of the stimulating electrodes 202, 204, and 206 is also connected to a VEG connector 218 through respective switches 220, 222, and 224. The operation of this system 200 is similar to that of system 100. When the system is used to sense heart activity, the switches 220, 222, and 224 are closed, and switches 210, 212, and 216 are opened. Conversely, when the system is used to defibrillate the heart, switches 220, 222, and 224 are opened, and switches 210, 212, and 216 are closed. Stimulating electrodes 202 and 206 are both high-potential electrodes due to their connection to the high-potential pick-up electrode 208. Thus, both of those stimulating electrodes receive electrical stimulating energy from the pick-up electrode 208, which passes through the heart to the low-potential stimulating electrode 204, then to the pick-up electrode 214, and on to ground through a low-potential defibrillation paddle, ground plate, or the like.

By using external pick-up electrodes 208 and 214, a much lower current can be used during defibrillation than is normally required when the defibrillation paddles are applied to the patient's body. This is due to the fact that the electrical energy is conducted directly to the stimulating electrodes 202 and 206, and thus the patient's heart, via respective conductive leads, rather than requiring the electrical energy to pass through the patient's body to the heart.

In the embodiments of FIGS. 7 and 8, the stimulating electrodes 106, 108, 202, 204, and 206 are preferably mounted on the inside surface of the suction membrane 24, or at some other similar location, such that when the cuff 12 grips the heart, the electrodes come into contact with the heart, thereby eliminating any motion artifact that would otherwise be generated if the electrodes moved relative to the heart. In this manner, the electrodes reliably and efficiently sense the heart's electrical activity, without the requirement of suturing, adhering, or otherwise connecting the electrodes directly to the heart.

In all of the above-described embodiments, the stimulating electrodes are preferably placed on the inside surface of the suction membrane 24. The electrodes are therefore preferably made sufficiently flexible to allow the suction membrane to easily conform to the shape of the heart, thereby assuring proper adherence of the cuff 12 to the heart.

From the foregoing, it will be apparent that the present invention provides an effective system for performing multiple heart-assisting functions. The system assists weak or failing hearts by increasing the compressive force of the heart's ventricles, and also applies electrical energy to the heart for defibrillation and other similar purposes. Moreover, the system can be used to also sense the heart's electrical activity for diagnostic purposes.

While the invention has been particularly shown and described with reference to illustrative embodiments thereof, it will be understood by those skilled in the art that various changes in form and details may be made therein without departing from the spirit and scope of the invention. Accordingly, it is not intended that the invention be limited, except as by the appended claims.

What is claimed is:

1. A system for defibrillating a heart, the system comprising:
    at least one pick-up electrode located inside a patient's body, the pick-up electrode being responsive to the application of external energy to the patient to collect at least a portion of the energy; and
    at least one stimulating electrode in electrical communication with the at least one pick-up electrode and disposed at a predetermined location adjacent the heart, the stimulating electrode being responsive to receipt of collected energy from the pick-up electrode to apply the energy to the heart.

2. The system of claim 1 further including a ventricular assist device adapted to be placed over at least a portion of the heart and operative to apply a compressive force on the ventricles of the heart to force the ventricles to contract, and wherein the stimulating electrode is connected to an interior surface of the ventricular assist device to contact the heart when the ventricular assist device is placed over the heart.

3. The system of claim 2, wherein the pick-up electrode is mounted on an exterior surface of the ventricular assist device.

4. The system of claim 2, wherein the pick-up electrode is spaced a preselected distance from the ventricular assist device.

5. The system of claim 1 further including plural pick-up electrodes and plural stimulating electrodes, the pick-up electrodes being electrically connected to the respective stimulating electrodes.

6. A defibrillation system for assisting a heart to pump and for defibrillating the heart, the system comprising:
    a ventricular assist device adapted to be placed over at least a portion of the heart and operative to apply a compressive force on the ventricles of the heart to force the ventricles to contract;
    at least one stimulating electrode connected to the ventricular assist device at a predetermined location thereon to be located adjacent to the heart when the ventricular assist device is placed over the heart; and
    at least one pick-up electrode electrically connected to the at least one stimulating electrode and adapted to be positioned at a predetermined location inside of a patient's body, the pick-up electrode being operative to collect externally applied energy and to conduct the externally applied energy to the stimulating electrode to defibrillate the heart.

7. The system of claim 6, wherein the stimulating electrode is connected to an interior surface of the ventricular assist device to contact the heart when the ventricular assist device is placed over the heart.

8. The system of claim 7, wherein the pick-up electrode is mounted on an exterior surface of the ventricular assist device.

9. The system of claim 6, wherein the pick-up electrode is mounted on an exterior surface of the ventricular assist device.

10. The system of claim 6 further including plural pick-up electrodes and plural stimulating electrodes, the pick-up electrodes being electrically connected to the respective stimulating electrodes.

11. The system of claim 6, wherein the pick-up electrode is spaced from the ventricular assist device.

12. A method of defibrillating a human heart, comprising:
    applying defibrillation energy to a patient from a location external to the patient;
    receiving the externally applied energy at one or more electrodes inside the patient's body; and
    conducting the received energy to one or more electrodes in contact with the patient's heart to apply the energy to the heart.

13. The method of claim 12, wherein the step of applying defibrillation energy includes using defibrillation paddles.

14. The method of claim 12, wherein the step of receiving the externally applied energy includes using a pair of external electrodes.

15. The method of claim 12, wherein the step of conducting the received energy includes using a pair of stimulation electrodes.

16. A method of assisting a heart to pump and of defibrillating the heart, comprising:

extending a ventricular assist device over at least a portion of the heart;

actuating the ventricular assist device to intermittently apply a compressive force on the ventricles of the heart to cause the ventricles to contract;

applying defibrillation energy to the patient from a location external to the patient;

receiving the externally applied energy at one or more electrodes inside the patient's body; and conducting the received energy to one or more electrodes in contact with the patient's heart to apply the energy to the heart.

17. The method of claim 16, wherein the step of applying defibrillation energy includes using defibrillation paddles.

18. The method of claim 16, wherein the step of receiving the externally applied energy includes using a pair of external electrodes.

19. The method of claim 16, wherein the step of conducting the received energy includes using a pair of stimulation electrodes.

20. A defibrillation system for assisting a heart to pump and for defibrillating the heart, the system comprising:

a ventricular assist device adapted to be placed over at least a portion of the heart and operative to engage at least a portion of the heart and to intermittently apply a compressive force on the ventricles of the heart to force the ventricles to contract, the ventricular assist device comprising a suction membrane operative to engage at least a portion of the heart; and at least one stimulating electrode in contact with the suction membrane and configured to be positioned in contact with the heart when the ventricular assist device is engaged to the heart, the stimulation electrode being responsive to the receipt of electrical energy to apply the energy to the heart.

21. The system of claim 20, wherein the stimulating electrode is connected to an external electrode via an electrical lead.

22. The system of claim 21, wherein the external electrode includes means for being located inside of the patient's body.

23. The system of claim 22, wherein the external electrode is mounted on an exterior surface of the ventricular assist device.

24. The system of claim 22, wherein the external electrode includes means for being positioned at a location inside of the patient's body and spaced from the ventricular assist device.

25. The system of claim 21, wherein the external electrode includes means for being located outside of the patient's body.

26. The system of claim 20, wherein the stimulating electrode is connected to a source of stimulating energy via an electrical lead.

27. The system of claim 20, wherein the stimulating electrode is connected to an interior surface of the suction membrane to contact the heart when the ventricular assist device is placed over the heart.

28. The system of claim 20 further including plural external electrodes and plural stimulating electrodes, the external electrodes being electrically connected to the respective stimulating electrodes.

29. The system of claim 20 further including at least two stimulating electrodes connected to the suction membrane of the ventricular assist device, and a VEG connector electrically connected to the respective stimulating electrodes to receive electrical activity signals from the stimulating electrodes.

30. A method of defibrillating a human heart, comprising:

providing a ventricular assist device which comprises a suction membrane and at least one stimulating electrode mounted at a predetermined location on the suction membrane;

extending the ventricular assist device over at least a portion of the heart;

creating at least a partial vacuum inside the suction membrane such that the suction membrane engages the heart and the at least one stimulating electrode is drawn into close proximity, or contact, with the heart;

delivering defibrillation energy to the at least one stimulating electrode to apply the energy to the heart.

31. The method of claim 30, wherein the step of creating at least a partial vacuum involves applying sufficient negative pressure in the interior of the suction membrane to securely engage the at least one stimulating electrode to the heart to at least substantially reduce translational movement between the electrode and the heart.

32. The method of claim 30, wherein the step of creating at least a partial vacuum involves applying sufficient negative pressure in the interior of the suction membrane to securely engage the at least one stimulating electrode to the heart to reduce the amount of energy required to defibrillate the heart.

* * * * *